United States Patent [19]
Poppas

[11] Patent Number: 5,929,044
[45] Date of Patent: Jul. 27, 1999

[54] PROTEIN SOLDER COMPOSITION AND METHOD OF USE

[75] Inventor: Dix P. Poppas, Larchmont, N.Y.

[73] Assignee: Cornell Research Foundation, Ithaca, N.Y.

[21] Appl. No.: 08/911,217

[22] Filed: Aug. 14, 1997

[51] Int. Cl.[6] .................................................. A61K 48/00
[52] U.S. Cl. ........................... 514/44; 514/2; 435/320.1; 435/325; 435/455; 435/458; 424/93.21; 602/2; 606/8; 606/213; 606/214
[58] Field of Search ..................... 514/44, 2; 435/172.3, 435/325, 320.1, 455, 458; 602/2; 606/8, 213, 214; 424/93.21; 536/23.1

[56] References Cited

U.S. PATENT DOCUMENTS

| | | | |
|---|---|---|---|
| 3,324,775 | 6/1967 | Rhee et al. | 525/54.2 |
| 5,209,776 | 5/1993 | Bass et al. | 106/24 |
| 5,292,362 | 3/1994 | Bass et al. | 016/221 |
| 5,573,934 | 11/1996 | Hubbell et al. | 435/177 |
| 5,661,132 | 8/1997 | Eriksson et al. | 514/44 |
| 5,674,703 | 10/1997 | Woo et al. | 435/69.1 |
| 5,713,891 | 2/1998 | Popas | 606/2 |
| 5,763,416 | 6/1998 | Bonadio et al. | 514/44 |
| 5,770,580 | 1/1998 | Ledley et al. | 514/44 |

FOREIGN PATENT DOCUMENTS

WO 91/04703  4/1991  WIPO.
WO 96/22054  7/1996  WIPO.
WO 96/38093  12/1996  WIPO.

OTHER PUBLICATIONS

Mastrangelo et al. (Seminars in Oncology, 1996, vol. 23, 1:4–21), Feb. 12, 1998.
Verma et al. (Nature, vol. 389, pp. 239242), Feb. 12, 1998.
Wagner (Nature, vol. 372: 333–335, 1994), Feb. 12, 1998.
Friedmann, *Scientiic American*, 96–105 (Jun. 1997).
Poppas et al., *Lasers in Surgery and Medicine,* 19, 360–368 (1996).
Poppas et al., *Lasers in Surgery and Medicine,* 19, 2–8, (1996).

*Primary Examiner*—Bruce R. Campbell
*Assistant Examiner*—Dave Trong Nguyen
*Attorney, Agent, or Firm*—Leydig, Voit & Mayer, Ltd.

[57] ABSTRACT

The present invention provides a composition comprising a protein solder, a bioactive compound, and a vehicle for delivering the bioactive compound into a target cell having a genome. The present invention also provides a method for delivering a bioactive compound into a target cell having a genome comprising (a) contacting a tissue with a composition comprising the protein solder, a bioactive compound, and a vehicle for delivering the bioactive compound into the target cell, and (b) exciting the protein solder to effect delivery of the bioactive compound into the target cell.

25 Claims, No Drawings

PROTEIN SOLDER COMPOSITION AND METHOD OF USE

TECHNICAL FIELD OF THE INVENTION

The present invention relates to a protein solder composition allowing for the delivery of bioactive compounds into target cells and a method for using same.

BACKGROUND OF THE INVENTION

The effectiveness of a variety of therapeutic procedures, including the use of pharmaceuticals, chemotherapy, and gene therapy, depends in large part on the ability to deliver bioactive compounds into target cells. Such bioactive compounds include, but are not limited to, proteins, nucleic acids, protein-nucleic acid fusion molecules, polysaccharides, metals, metal ions, and synthetic organic molecules.

Because the efficacy of a variety of therapeutic procedures derives in large part from the ability to deliver bioactive compounds into target cells, the delivery of bioactive compounds into non-targeted cells can have grave consequences for the patient being treated. Specifically, delivery of bioactive compounds into non-targeted cells can create a multitude of side effects which may outweigh any benefits realized from the application of the therapeutic procedure. Furthermore, for a finite amount of a bioactive compound, the effective concentration of the bioactive compound in target cells is reduced as a result of delivering the bioactive compound into non-targeted cells.

Two conventional methods for delivering bioactive compounds into target cells illustrate the difficulty surrounding the delivery of genetic material into target cells without the concomitant introduction of genetic material into non-targeted cells. Viral vectors and liposomes can be utilized as a means of delivering therapeutic genetic material into target cells. Ordinarily, the viral vectors and/or liposomes are injected directly into the bloodstream of the patient or are combined ex vivo with cells which are removed from the patient and which are subsequently returned to the patient upon being genetically altered. See generally, *Scientific American,* June 1997, pp. 96–120. However, both of the foregoing mechanisms result in delivery of genetic material into non-targeted cells. Injection into the bloodstream allows the viral vectors to infect and the liposomes to fuse with non-targeted cells because the viral vectors and/or liposomes are dispersed throughout the patient's body. Similarly, in the absence of a method by which target cells can be isolated from a mixture of target and non-target cells, the ex vivo combination of viral vectors and/or liposomes with cells removed from the patient also will result in delivery of genetic material into non-targeted cells. Therefore, the value of the above delivery methods is limited to the extent that both methods lead to the introduction of genetic material into non-targeted cells and, consequently, attenuate the effectiveness of the underlying therapeutic procedure.

In view of the foregoing problems, there exists a need for a method by which bioactive compounds can be delivered into cells in a site-specific fashion. The present invention provides for such a delivery method and associated compositions useful therefor. These and other advantages of the present invention, as well as additional inventive features, will be apparent from the description of the invention provided herein.

BRIEF SUMMARY OF THE INVENTION

The present invention provides a composition comprising a protein solder, a bioactive compound, and a vehicle for delivering the bioactive compound into a target cell having a genome. The present invention also provides a method for delivering a bioactive compound into a target cell having a genome comprising (a) contacting a tissue comprising the target cells with a composition comprising a protein solder, a bioactive compound, and a vehicle for delivering the bioactive compound into the target cell, and (b) exciting the protein solder to effect delivery of the bioactive compound into the target cell.

The invention may best be understood with reference to the following detailed description of the preferred embodiments.

DESCRIPTION OF THE PREFERRED EMBODIMENTS

The present invention provides a protein solder composition as well as a method which utilizes such a protein solder composition to deliver a bioactive compound into a target cell having a genome. The present inventive composition comprises a protein solder, a bioactive compound, and a vehicle for delivering the bioactive compound into a target cell having a genome. The present inventive method for delivering a bioactive compound into a target cell having a genome comprises (a) contacting a tissue comprising the target cells with a composition comprising a protein solder, a bioactive compound, and a vehicle for delivering the bioactive compound into the target cell, and (b) exciting the protein solder to effect delivery of the bioactive compound into the target cell.

Any suitable protein solder can be utilized in the context of the present invention. Protein solders suitable for contact with tissues and suitable for various forms of excitation are well known in the art. See generally, WO 96/38093 (Poppas et al.). While any suitable protein solder can be used in the context of the present invention, preferred solders are proteins such as albumin, fibrinogen, and collagen, which are denatured upon exposure to localized heating and which are further capable of cross-linking to each other and to the adjacent tissue to which the protein solder is contacted. While the protein solder itself can act as a vehicle for the delivery of bioactive compounds into targeted cells, in the context of the present invention, the protein solder functions as a matrix which fixes to the targeted cells a bioactive compound and a vehicle for delivering the bioactive compound. For example, the protein solder can act as a vehicle for delivering naked DNA, which is known to inefficiently enter cells on its own accord, into targeted cells. In contrast, in the context of the present invention, the protein solder functions as a matrix to fix some other vehicle (e.g., a liposome or vector such as a virus) which will deliver a bioactive compound into the targeted cells.

Any suitable vehicle can be utilized in the context of the present invention. Suitable vehicles include, but are not limited to, liposomes and vectors such as viruses. The liposomes can be of any suitable shape and can be of any suitable size. Suitable liposome shapes include tubular and spherical configurations. While the liposome can be of any suitable size, typically, liposomes will be large enough to encapsulate particular bioactive compounds. Preferably, the internal diameter of the liposome will be greater than about 0.025 $\mu$m; more preferably, greater than about 0.1 $\mu$m; and most preferably, greater than about 2.0 $\mu$m. Furthermore, the lipids comprising the liposomes can be modified so as to ease encapsulation of particular bioactive compounds. For example, cationic lipids can be used in liposome formations so as to ease the encapsulation of negatively charged nucleic acids. Liposome surfaces also can be modified to alter the efficiency with which liposomes fuse with target cells. For example, specialized proteins or protein fragments resembling those that target viruses to particular cell types can be incorporated into the outer surface of the liposome. Alternatively, viral-like membrane fusion proteins can be incorporated into the outer surface of the liposome to facilitate the survival and functioning of the bioactive compound in the targeted cells. Formation of liposomes with bioactive compounds encapsulated therein is well known in the art.

While any suitable virus can be used as a vehicle in the context of the present invention, the virus is preferably an adenovirus, retrovirus, adeno-associated virus, herpesvirus, alphavirus, or poxvirus; is more preferably a retrovirus, adenovirus, or adeno-associated virus; and is most preferably an adenovirus. Furthermore, in order to vary the binding specificity of the chosen virus to the targeted cell or to facilitate the survival and functioning of the bioactive compound in the targeted cells, the chosen virus can be altered so as to replace or modify its natural envelope proteins, or, alternatively, new proteins or parts of proteins can be added to existing envelopes.

Any suitable biologically active compound can be used as a bioactive compound in the context of the present invention. While any suitable bioactive compound can be selected for use in the context of the present invention, the bioactive compound is preferably a protein, nucleic acid, protein-nucleic acid fusion molecule, polysaccharide, metal, metal ion, or synthetic organic molecule; and more preferably, a nucleic acid. Furthermore, the nucleic acid can be, for example, a cDNA encoding a protein, an antisense oligonucleotide, or a catalytic RNA. Depending on the sequence of the cDNA and the vehicle used to deliver the cDNA into the target cells, the cDNA, once delivered into the target cells, can either integrate into the target cells' genome or exist within the target cells without integrating into the target cells' genome. Nuclear targeting signals also can be attached to cDNA in order to direct the cDNA to the targeted cells' nuclei and, therefore, raise the effective concentration of the nuclear cDNA.

The present inventive composition comprises the protein solder, bioactive compound, and vehicle. The targeted tissue can be contacted with the composition in any suitable manner. The tissue can be contacted with each separate element (e.g., the protein solder, the vehicle, and the bioactive compound) of the composition in piecemeal, or, alternatively, two or more elements of the composition can be combined prior to contacting the tissue while the other elements of the composition can separately contact the tissue. Furthermore, the tissue can be contacted with one or more elements of the composition in any combination and in any order. Preferably, the protein solder, vehicle, and bioactive compound are combined prior to contacting the tissue with the composition.

The present invention provides a method for delivering the bioactive compound into target cells having a genome comprising (a) contacting a tissue comprising the target cells with a composition comprising the protein solder, the bioactive compound, and the vehicle for delivering the bioactive compound into the target cells, and (b) exciting the protein solder to effect delivery of the bioactive compound into the target cells. The tissue in contact with the composition can be any suitable tissue comprising the target cells to which the bioactive compound is to be delivered. Furthermore, the tissue can be contacted with the composition utilizing any suitable means to do so. For example, the tissue can be contacted with the composition by brushing, spraying, or dripping the composition on to the tissue.

As previously stated, the tissue can be contacted with the protein solder either separately or in combination with the other elements of the composition. Following contact of the tissue with the protein solder, the protein solder is excited so as to induce localized heating, denaturation of the proteins comprising the protein solder, and cross-linking of the proteins to each other and to the tissue contacted with the protein solder. In other words, upon being excited, the protein solder becomes fixed to the tissue to which it makes contact. While not wishing to be bound to any particular theory, it appears that upon degradation of the cross-linked proteins, the vehicles for delivering the bioactive compounds to the target cells are free to do so. Because both the vehicle and bioactive compound are effectively concentrated at the target cells due to fixation on the tissue by the excited protein solder, delivery of the bioactive compound into target cells is enhanced and delivery of the bioactive compound into non-target cells is reduced relative to conventional delivery methods.

Any suitable means can be used to excite the protein solder. Preferably, either light energy or radiofrequency energy is used to excite the protein solder, and, more preferably, light energy (e.g., from a laser source) is used to excite the protein solder. The appropriate conditions surrounding the excitation of the protein solder are well known to those of ordinary skill in the art.

The following example illustrates the ability of the present invention to deliver a bioactive combound (DNA having a gene) into cells. The example is included purely for illustrative purposes and should not be construed to limit the scope of the invention in any respect.

50% human albumin was supplemented with AD5 beta-galactosidase adenovirus which contained a gene sequence for β-galactosidase. The supplemented protein solder was placed into 96 well petri dishes, resulting in a titer of $1 \times 10^7$ viruses per well, and lased using a 1.32 $\mu$m laser at a temperature of between 60° C. and 100° C. Laser exposure times varied between 10 seconds and 2 minutes. Following the laser denaturation of the protein solder, target CA549 human lung cancer cells, numbering 3000 per well, were allowed to grow on the protein solder in the presence of DMEM growth media, with and without fetal calf serum, for 48 hours. After 48 hours, the CA549 human lung cancer cells were treated with a standard X-gal stain, and it was confirmed that the gene for β-galactosidase had been delivered into the target lung cells.

All of the references cited herein, including patents, patent applications, and publications, are hereby incorporated in their entireties by reference.

While this invention has been described with an emphasis upon preferred embodiments, it will be obvious to those of ordinary skill in the art that variations of the preferred embodiments may be used and that it is intended that the invention may be practiced otherwise than as specifically described herein. Accordingly, this invention includes all modifications encompassed within the spirit and scope of the invention as defined by the following claims.

What is claimed is:

1. A composition comprising a protein solder, a bioactive compound, and a vehicle for delivering said bioactive compound into a target cell having a genome, wherein said vehicle is a virus or a liposome.

2. The composition of claim 1, wherein said virus is selected from the group consisting of adenoviruses, retroviruses, adeno-associated viruses, herpesviruses, alphaviruses, and poxviruses.

3. The composition of claim 2, wherein said virus is selected from the group consisting of adenoviruses, retroviruses, and adeno-associated viruses.

4. The composition of claim 3, wherein said virus is an adenovirus.

5. The composition of claim 1, wherein said bioactive compound is selected from the group consisting of proteins, nucleic acids, protein-nucleic acid fusion molecules, polysaccharides, metals, metal ions, and synthetic organic molecules.

6. The composition of claim 5, wherein said bioactive compound is a nucleic acid.

7. The composition of claim 6, wherein said nucleic acid is a cDNA encoding a protein.

8. The composition of claim 6, wherein said nucleic acid is an antisense oligonucleotide.

9. The composition of claim 6, wherein said nucleic acid is a catalytic RNA.

10. The composition of claim 1, wherein said bioactive compound is a nucleic acid and said vehicle is a virus.

11. The composition of claim 1, wherein said bioactive compound is a nucleic acid and said vehicle is a liposome.

12. A method for delivering a bioactive compound into a target cell having a genome comprising (a) contacting a tissue comprising said target cell with a composition comprising a protein solder, a bioactive compound, and a vehicle for delivering said bioactive compound into said target cell, wherein said vehicle is a virus or a liposome, and (b) exciting said protein solder to effect delivery of said bioactive compound into said target cell.

13. The method of claim 12, wherein said protein solder is excited with light energy.

14. The method of claim 12, wherein said protein solder is excited with radiofrequency energy.

15. The method of claim 12, wherein said virus is selected from the group consisting of adenoviruses, retroviruses, adeno-associated viruses, herpesviruses, alphaviruses, and poxviruses.

16. The method of claim 15, wherein said virus is selected from the group consisting of adenoviruses, retroviruses, and adeno-associated viruses.

17. The method of claim 16, wherein said virus is an adenovirus.

18. The method of claim 12, wherein said bioactive compound is selected from the group consisting of proteins, nucleic acids, protein-nucleic acid fusion molecules, polysaccharides, metals, metal ions, and synthetic organic molecules.

19. The method of claim 18, wherein said bioactive compound is a nucleic acid.

20. The method of claim 19, wherein said nucleic acid is a cDNA encoding a protein.

21. The method of claim 20, wherein said cDNA is integrated into the genome of said target cell.

22. The method of claim 19, wherein said nucleic acid is an antisense oligonucleotide.

23. The method of claim 19, wherein said nucleic acid is a catalytic RNA.

24. The method of claim 12, wherein said bioactive compound is a nucleic acid and said vehicle is a virus.

25. The method of claim 12, wherein said bioactive compound is a nucleic acid and said vehicle is a liposome.

* * * * *